United States Patent

Cartmell et al.

[11] Patent Number: 5,204,110
[45] Date of Patent: * Apr. 20, 1993

[54] HIGH ABSORBENCY HYDROGEL WOUND DRESSING

[75] Inventors: James V. Cartmell, Xenia; Wayne R. Sturtevant, Centerville; Michael L. Wolf, West Milton; Michael J. Allaire, Cincinnati, all of Ohio

[73] Assignee: NDM Acquisition Corp., Minneapolis, Minn.

[*] Notice: The portion of the term of this patent subsequent to Oct. 22, 2008 has been disclaimed.

[21] Appl. No.: 838,464

[22] Filed: Feb. 19, 1992

Related U.S. Application Data

[63] Continuation-in-part of Ser. No. 517,837, Apr. 2, 1990, Pat. No. 5,115,801.

[51] Int. Cl.$^5$ ............................................. A61F 13/00
[52] U.S. Cl. .................................. 424/443; 424/445; 424/447; 602/48; 602/57; 604/304
[58] Field of Search ............... 424/443, 447, 445; 604/304; 602/48, 57

[56] References Cited

U.S. PATENT DOCUMENTS

| | | | |
|---|---|---|---|
| 3,526,224 | 6/1967 | Potts | 128/155 |
| 3,543,750 | 1/1968 | Meizanis | 128/154 |
| 3,579,628 | 5/1971 | Gander | 424/28 |
| 4,061,618 | 12/1977 | Stanley | 260/29.2 |
| 4,226,232 | 10/1980 | Spence | 128/156 |
| 4,393,048 | 7/1989 | Mason, Jr. | 424/132 |
| 4,460,369 | 7/1984 | Seymour | 604/897 |
| 4,517,326 | 5/1985 | Cordts | 524/310 |
| 4,538,603 | 9/1985 | Pawelchak | 128/156 |
| 4,595,001 | 6/1986 | Potter | 128/156 |
| 4,657,006 | 4/1987 | Rawlings | 128/156 |
| 4,669,458 | 6/1987 | Abraham | 604/180 |
| 4,704,119 | 11/1987 | Shaw | 604/897 |
| 4,743,249 | 5/1988 | Loveland | 424/447 |
| 4,747,401 | 5/1988 | Potter | 128/156 |
| 4,753,232 | 6/1988 | Ward | 128/156 |
| 4,759,354 | 7/1988 | Quarfoot | 128/156 |
| 4,909,244 | 3/1990 | Quarfoot | 128/156 |
| 4,921,704 | 5/1990 | Fabo | 424/446 |
| 5,059,424 | 11/1991 | Cartmell | 424/443 |
| 5,106,629 | 4/1992 | Cartmell | 424/445 |

*Primary Examiner*—Thurman K. Page
*Assistant Examiner*—D. Gabrielle Phelan
*Attorney, Agent, or Firm*—Killworth, Gottman, Hagan & Schaeff

[57] ABSTRACT

A flexible burn dressing product contains a high absorbency hydrogel material in a gel phase. The hydrogel material is formed from a hydrogel composition for use in a wound dressings. The hydrogel composition is formed from a mixture comprising: (a) from about 0% to about 90% by weight polyhydric alcohol selected from the group consisting of polypropylene glycol, polyethylene glycol and glycerine; (b) from about 6% to about 60% by weight aliphatic diisocyanate terminated prepolymer based on polyols containing more than about 40% polyethylene oxide and having an isocyanate content of about 3% by weight; (c) from about 4% to about 40% by weight polyethylene oxide based polyamine; (d) up to about 2% by weight sodium chloride; and (e) the balance water. Such a hydrogel material provides a highly absorbent material capable of retaining large amounts of wound exudate, thereby rendering it very suitable for use in wound dressings.

19 Claims, 4 Drawing Sheets

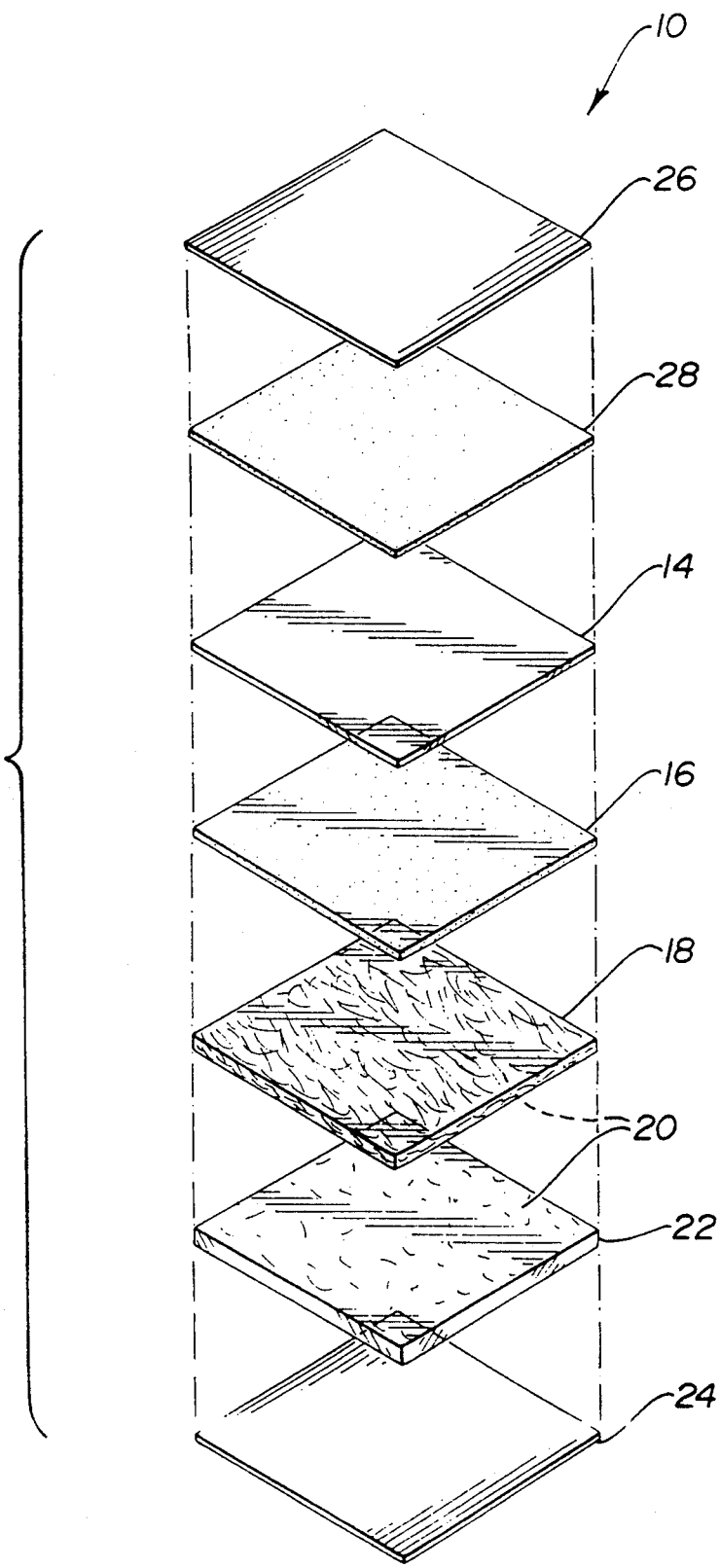

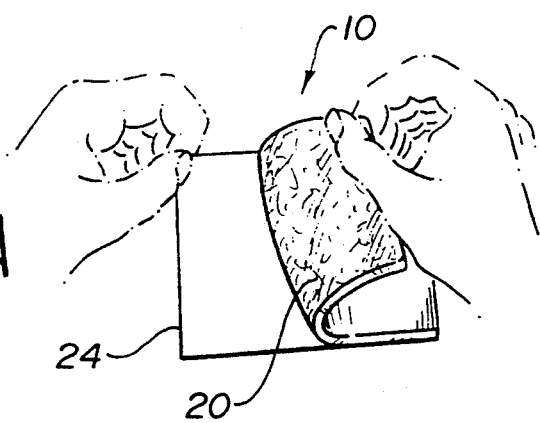
FIG-4A
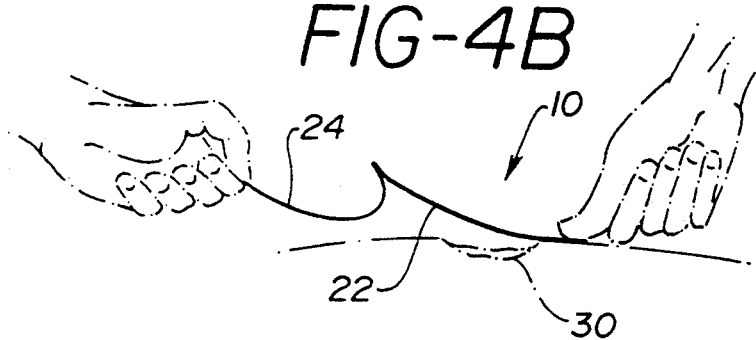
FIG-4B
FIG-4C
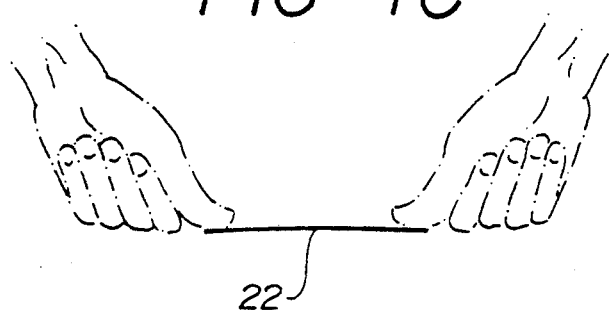
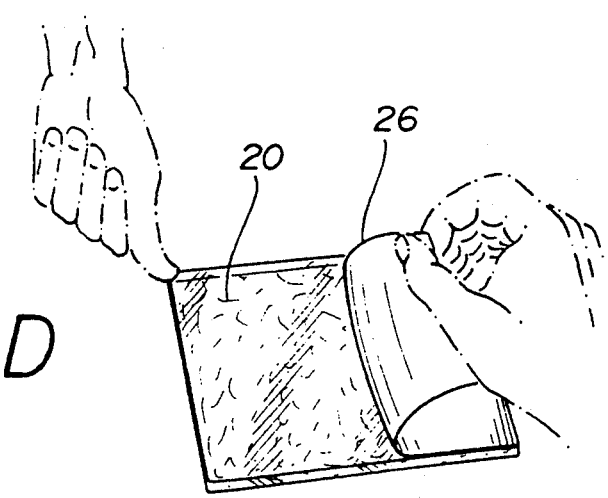
FIG-4D

HIGH ABSORBENCY HYDROGEL WOUND DRESSING

CROSS REFERENCE TO RELATED APPLICATIONS

The present application is a continuation-in-part of copending U.S. application Ser. No. 517,837, filed Apr. 2, 1990, now allowed U.S. Pat. No. 5,115,801, entitled "HYDROGEL BURN DRESSING."

BACKGROUND OF THE INVENTION

The present invention generally relates to wound dressings and, more particularly, to a highly absorbent hydrogel for use in wound dressing products which are particularly useful in the active therapy of thermal, chemical, electrical, and similar wounds conventionally classified as "burns."

Burn injuries require a unique combination of therapy and dressing because the physiologic functions of the skin are absent or, at best, materially impaired. Body fluids and their essential components are continuously lost. The natural barrier characteristics normally provided by one's skin, of preventing invasion of harmful micro-organisms and other noxious agents, are no longer functional. Potentially fatal infections are a continuous serious threat to burn patients. The debris reservoir of necrotic tissue saturated with seeping wound exudate remains on the wound site, harboring and nourishing agents of infection whose presence and by-products interfere with the regeneration of viable, functioning, epithelial tissue having skin organ properties.

The basic tenets of therapy required to treat burns are specifically directed toward providing and improving the impaired physiologic functions of the skin. Of initial concern is the removal of the necrotic products of injury. Also of great importance is providing a barrier to bacterial invasion from the environment while controlling the contamination already present. Finally, burn therapy is directed toward stemming the loss of vital body fluids.

Burn injuries and the like have been treated at various stages by application of sterile coverings in the form of pastes or creams, gauze wrappings, natural and synthetic membranes, films, or sponges. Except in the case of skin grafting, the approach has been to prevent adhesion of the covering materials to the wound site while encouraging adhesion of the burn exudate to the covering materials.

One existing burn exudate absorption method is to apply a polyurethane polymer composition to the burn site. As disclosed in Gould, U.S. Pat. No. 4,156,066, and Gould, U.S. Pat. No. 4,156,067, issued May 22, 1979, a polyurethane polyether resin may be applied to a burn as a powder. However, powder tends to attract fluids from the burn wound and deteriorates as the wound fluids are absorbed, resulting in lumping and uneven application. Additionally, such deteriorated lumps are difficult to remove from a burn site without damaging new cell tissue at the burn site.

A burn dressing which attempts to minimize fluid loss from the burn site is disclosed in U.S. Pat. No. 3,648,692, issued to Wheeler on Mar. 14, 1972. The Wheeler burn dressing discloses an open cell foam material which can be applied directly to a burn wound site. However, while it is desirable to stem the loss of vital body fluids from the already weakened patient, the Wheeler burn dressing eliminates or minimizes the loss of all fluids, even fluids contaminated with necrotic tissue, from the burn site. Also, new cell tissue forming at the burn site may adhere to the sponge-like material, making it difficult to remove the burn dressing from the burn site without damaging new cell tissue. Consequently, the Wheeler burn dressing serves merely as a sedentary covering for allowing the burn to heal, rather than actively expediting the healing.

Aqueous moisture absorbing materials, such as a polyethylene glycol liquid curing agent as disclosed in Spence, U.S. Pat. No. 4,226,232, issued Oct. 7, 1980, are easier to remove from the wound site, but cannot be sterilized by irradiation due to the formation of free radicals within the aqueous material. Another aqueous absorbing material used to absorb wound exudate, hydrophilic polymer, is disclosed in Rawlings et al, U.S. Pat. No. 4,657,006, issued Apr. 14, 1987. In the Rawlings et al reference, a wound dressing is described which comprises a hydrophilic polymer having moisture vapor permeability characteristics. A problem with the Rawlings et al wound dressing is that the wound exudate absorbed by the hydrophilic polymer hardens the polymer, allowing pockets to develop between the polymer and the wound, providing an excellent environment for bacteria proliferation.

Known aqueous moisture absorbing wound dressing systems have additional problems, in that the aqueous material is generally contained in the center portion of a wound dressing, with a bulky adhesive border, such as a foam border. Problems with such borders include decreased comfort, conformity and adhesion as well as the existence of a "lifting edge" that can catch on clothes or bed sheets, thereby exposing the wound to bacteria and infection. In addition, burn sites typically have very little healthy skin to which such a dressing may be adhered.

An existing method of overcoming the problems associated with bulky wound dressings is disclosed in Potts, U.S. Pat. No. 3,526,224 issued Sep. 1, 1970. The Potts reference discloses a wound dressing comprised of an elastomeric polyurethane film which acts as a second skin during the wound healing process. One problem with the Potts wound dressing, however, is that the "second skin" requires surgery to remove it after the wound has healed.

Hence, it would be desirable to provide a burn dressing which eliminates or minimizes vital and healthy fluid loss from a burn site while simultaneously removing contaminated or infected wound fluids. It would also be desirable to provide a burn dressing product which could be readily available for application to a burn wound. It would further be desirable to provide such a burn dressing which contains wound debridement characteristics and which absorbs large quantities of wound exudate yet does not adhere to the burn site, thereby providing means to expedite healing. In addition, it would be desirable to provide a burn dressing which could be removed neatly and, more importantly, without adhering to the new cell tissue forming at the burn site. Finally, it would be desirable to provide such a burn dressing product which could be comfortably applied to any area on a body.

SUMMARY OF THE INVENTION

The present invention meets these needs by providing a highly absorbent hydrogel material which readily absorbs larger quantities of wound exudate when compared with those materials used in the past. Furthermore, the present invention provides a thin-film burn dressing containing such a hydrogel material, partially impregnated in a reticulated layer which may be of any suitable material including foam, scrim or non-woven material. The present invention also provides a method of manufacture and application of a burn dressing product which includes the burn dressing. The burn dressing product herein can be manufactured to any desirable size to provide a wound debridement dressing for any size burn site. The burn dressing herein is adhesive only to the extent that exuding wound fluids are absorbed, and non-adhesive upon removal from the burn site.

In accordance with one aspect of the invention, a highly absorbent hydrogel composition for use in a wound dressing is provided. The hydrogel material is formed from a mixture comprising: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. Such a hydrogel material provides a highly absorbent material capable of retaining large amounts of wound exudate, thereby rendering it very suitable for use in wound dressings. The hydrogel material in accordance with the invention is especially useful in the treatment of burns.

The burn dressing product of the present invention comprises a burn dressing which includes a bacterial barrier layer having a first side and a second side; a bonding layer, the bonding agent positioned on the first side of the bacterial barrier layer; a reticulated layer having a first side and a second side, the reticulated layer being impregnated with a hydrogel material; and a hydrogel material layer on the first side of the impregnated layer. The burn dressing product further comprises a release liner overlying the hydrogel material layer and secured to the first side of the impregnated layer by means of the hydrogel material layer.

A further embodiment of the burn dressing product may include a dimensionally stable backing member having an adhesive layer, the backing member secured to the second side of the bacterial barrier layer by means of the adhesive layer. In a preferred embodiment, the bacterial barrier layer comprises a polyurethane material, the release liner is silicone coated, and the bonding layer comprises a medical grade acrylic adhesive. However, the bonding layer may be any suitable bonding means such as adhesive or flame bonding. Also, the hydrogel material of the burn dressing product comprises from about 15% to about 30% by weight of a polyhydric alcohol, from about 8% to about 14% by weight of an isophoronediisocyanate terminated prepolymer, from about 5% to about 10% by weight of a polyethylene oxide based diamine, up to about 1% by weight of a salt, and the balance water.

The present invention also provides a method of manufacturing the burn dressing product. Initially, a release liner, a reticulated layer such as foam, scrim, or non-woven material, and a bacterial barrier layer are provided, each layer having a first side and a second side. The first side of the bacterial barrier layer is then coated with a bonding layer, after which the second side of the reticulated layer is bonded to the first side of the release liner, wherein the bonding layer is located between the reticulated layer and the release liner. The reticulated layer is impregnated with a hydrogel material, the hydrogel material forming a smooth hydrogel layer on the first side of the impregnated layer. The second side of the release liner is applied to the first side of the impregnated layer, wherein the smooth hydrogel material layer is located between the impregnated layer and the release liner.

Since the impregnated layer and aqueous hydrogel are extremely flexible and pliable, the method of manufacturing the burn dressing product may further include the step of providing a dimensionally stable backing member to maintain the burn dressing in its desired shape until the burn dressing product is applied to a burn site. The dimensionally stable backing member is applied to the second side of the bacterial barrier layer, wherein an adhesive layer is located between the second side of the bacterial barrier layer and the dimensionally stable backing member. In a preferred embodiment of the invention, the bonding layer preferably has stronger bonding qualities than the adhesive layer so as to allow removal of the dimensionally stable backing member from the bacterial barrier layer after application of the burn dressing product to the burn, while maintaining adhesion between the hydrogel material layer and the skin of a patient.

Finally, the present invention provides a method of application of the burn dressing product described above. When the burn dressing product is to be applied to a burn site, the release liner is partially removed to expose the hydrogel material layer so the hydrogel can contact the burn site. The burn dressing product is then applied directly over the burn site in a rolling motion, while continuing to remove the release liner until the release liner is completely removed and the burn dressing completely covers the burn site.

Directly contacting the burn is the hydrogel material layer, where it creates a bio-compatible, bacterial protective, fluid absorbing, cushioned skin-like media to facilitate the healing process. Once the burn dressing product has been placed on the burn site, then the dimensionally stable backing member can be removed. The result is a burn dressing containing a bio-compatible, non-irritating, fluid absorbing, skin-like media hydrogel material. Conformity and, more importantly, bacterial protection is improved since there is no "lifting edge" to catch on clothing or bed sheets.

The hydrogel material has healing and absorbing qualities and is preferably a saline solution in an aqueous gel phase, which is impregnable within the reticulated layer. The gel consistency of the hydrogel material creates a bond between the burn dressing and the burn site without creating an actual adhesive attachment that would damage new cell tissue upon removal. An advantage of the gel hydrogel is that it will absorb exudating burn wound fluids. Additionally, it permits clean and neat removal of the burn dressing when the burn heals or the dressing is changed. Finally, since the hydrogel material is transparent, it is possible to inspect the burn site without removing the burn dressing, provided the other layers of the burn dressing product are also transparent.

It is an object of the present invention to provide a burn dressing product containing an aqueous hydrogel substance which is particularly advantageous when used to dress burn sites, by providing a skin-like media which is bio-compatible, non-irritating, fluid absorbing, and bacterial protective; to provide a burn dressing which is more flexible and less bulky than existing dressings; to provide a burn dressing which will not adhere to new cell tissue when it is removed; and to provide a burn dressing product with the above features that is readily available for application to a burn site. Other objects and advantages of the invention will be apparent from the following description, the accompanying drawings, and the appended claims.

BRIEF DESCRIPTION OF THE DRAWINGS

FIG. 3 is an exploded view, illustrating the layers which form the preferred embodiment of the burn dressing product; and FIGS. 4A through 4D illustrate the preferred method of application of the burn dressing product of the present invention.

DETAILED DESCRIPTION OF THE INVENTION

The present invention relates to wound dressings and more particularly, to a highly absorbent hydrogel wound dressing which finds utility in many wound dressings including burn dressings for application to burn sites. The burn dressing product is comprised of a burn dressing and a release liner. The invention also includes a method of manufacture and a method of application for the disclosed burn dressing product.

Figure 1:
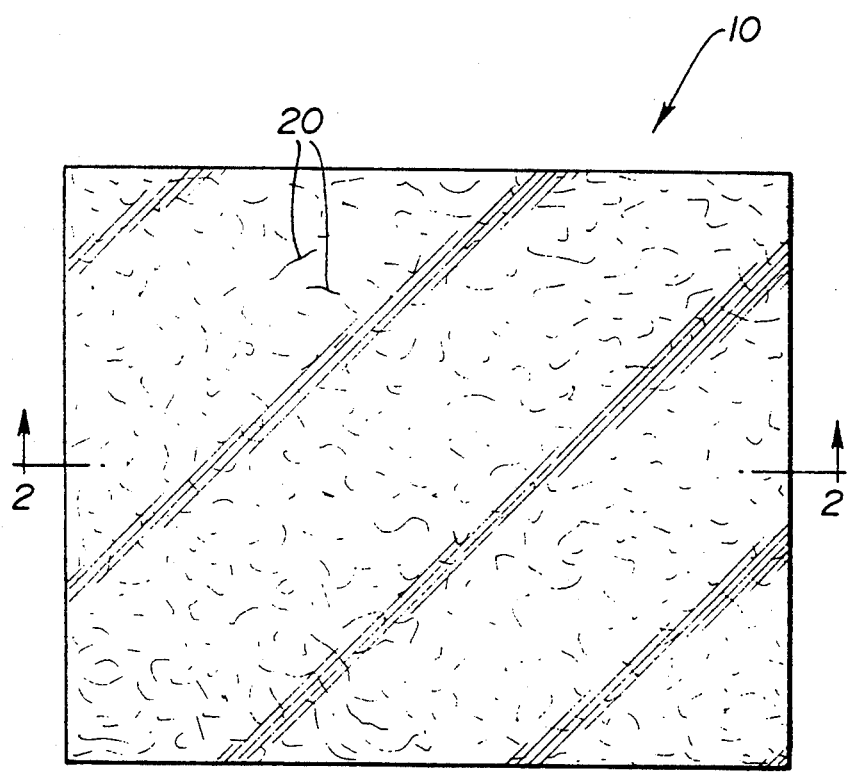
FIG. 1 is a plan view of the burn dressing product.

The burn dressing product 10 of the present invention is illustrated in FIGS. 1, 2A, 2B, and 3. Although the burn dressing product 10 is shown in FIG. 1 as having a rectangular shape, it may be any of a variety of desirable shapes. The burn dressing product 10 is composed of several layers including a wound dressing 12, as illustrated by the cross-sectional view of FIG. 2A and the exploded view of FIG. 3.

Figure 2A:
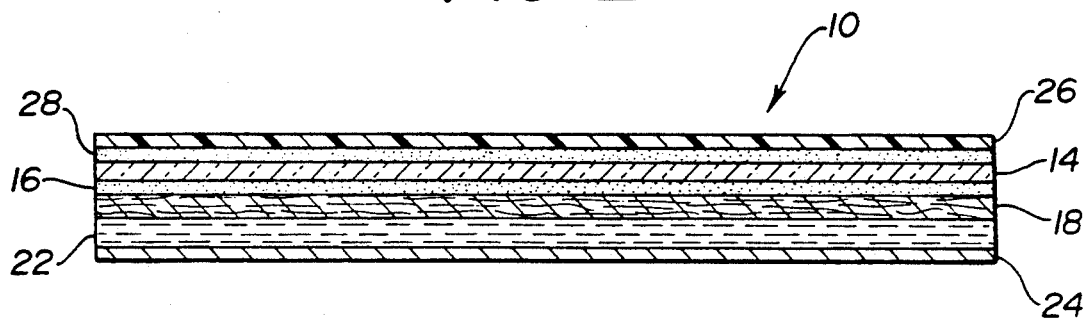
FIGS. 2A and 2B are cross-sectional views of the burn dressing product and the burn dressing, respectively, of FIG. 1 taken along line 2—2.
Figure 2B:
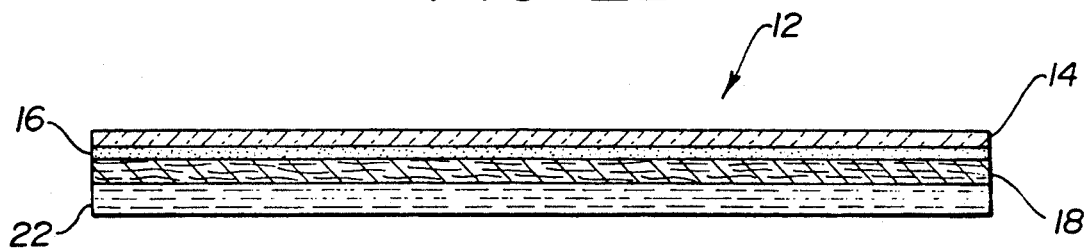

Referring now to FIG. 2A, the burn dressing product 10 is illustrated in cross-section, taken along line 2—2 of FIG. 1. The burn dressing product 10 includes a bacterial barrier layer 14, preferably of polyurethane. The bacterial barrier layer 14 has a first side and a second side, the first side being coated with a bonding agent to form bonding layer 16. The bonding layer 16 preferably comprises a medical grade acrylic adhesive, but may be any suitable bonding means including flame bonding. Attached to the bacterial barrier layer 14 via the bonding layer 16 is a reticulated layer 18, which layer 18 may be any suitable reinforcing material such as reticulated foam, scrim, or non-woven material, the layer 18 having a first side and a second side. The reticulated layer 18 is preferably absorbent enough to permit a hydrogel material 20 to be impregnated in the reticulated layer 18. A hydrogel material layer 22, which is discussed more fully below, is then secured by bonding or other means to the first side of the impregnated layer 18. Finally, a release liner 24, preferably silicone coated, overlies the hydrogel material layer 22 and is secured to the first side of the impregnated layer 18 by means of the hydrogel material layer 22. The bacterial barrier layer 14, the bonding layer 16, the impregnated layer 18, and the hydrogel material layer 22 comprise the wound dressing 12, as illustrated in FIG. 2B.

The combination of the impregnated layer 18 and the hydrogel material layer 22 is particularly advantageous for use on burn wounds. The impregnated layer 18 provides a cushion to protect the burn site from external trauma, but does not directly contact the burn site. Instead, to avoid having new cell tissue adhere to the impregnated layer 18, the smooth, gel hydrogel material layer 22 directly contacts the wound.

In a further embodiment, the burn dressing product 10 may include a dimensionally stable backing member 26, illustrated in FIGS. 2A and 3. The backing member 26 is secured to the second side of the bacterial barrier layer 14 by means of an adhesive layer 28. Also in a preferred embodiment of the invention, the bonding layer 16, located between the bacterial barrier layer 14 and the impregnated layer 18, has stronger bonding qualities than the adhesive layer 28, located between the bacterial barrier layer 14 and the dimensionally stable backing member 26. Such a construction allows removal of the dimensionally stable backing member 26 from the burn dressing 12 while maintaining the adhesion between the bacterial barrier layer 14 and the impregnated layer 18.

The present invention provides a method of manufacturing the wound dressing product 10. In the manufacturing method of the present invention, the release liner 24, the impregnated layer 18, and the bacterial barrier layer 14 are provided, each having a first side and a second side. Since the impregnated layer and aqueous hydrogel are pliable, the method of manufacturing the burn dressing product 10 may further include the step of providing the dimensionally stable backing member 26, having a first side and a second side, to maintain the burn dressing 12 in its desired shape until the burn dressing product 10 is applied to a burn site. The first side of the bacterial barrier layer 14 is coated with the bonding agent of the bonding layer 16 and the first side of the dimensionally stable backing member 26 is coated with the adhesive layer 28, which is illustrated in FIGS. 2A and 3. The second side of the bacterial barrier layer 14, if used in the manufacture of the burn dressing, is then laminated to the first side of the dimensionally stable backing member 26, wherein the adhesive layer 28 is located between the bacterial barrier layer 14 and the dimensionally stable backing member 26, as can be seen in FIG. 2A.

Once the layers of the burn dressing product 10 are manufactured, the reticulated layer 18 is impregnated with a clear, gel aqueous material 20, preferably hydrogel, which forms a smooth hydrogel material layer 22 on the first side of the impregnated layer 18. After the hydrogel material 20 has been impregnated in the reticulated layer 18, the second side of the release liner 24 is applied to the first side of the hydrogel material layer 22.

Preferably, the hydrogel material 20 is formed from an aqueous mixture of polyhydric alcohol, aliphatic diisocyanate terminated prepolymer, polyethylene oxide based polyamine and sodium chloride. Such a hydrogel material provides a highly absorbent material capable of retaining large amounts of wound exudate, thereby rendering it very suitable for use in wound dressings. Preferably, the polyhydric alcohol is selected from the group consisting of polypropylene glycol, polyethylene glycol and glycerine. In addition, it is preferable that the aliphatic diisocyanate be isophoronediisocyanate or similar diisocyanate while the polyamine is preferably a diamine. By forming the hydrogel layer 20 from the aforementioned aqueous mixture, the burn dressing product 10 or other type of wound dressing remains intact as it absorbs wound exudate from the wound. Furthermore, the hydrogel material 20 does not adhere or stick to the wound which allows for easy removal of the burn dressing product 10. Additionally, the biocompatibility of the hydrogel material 20 within the wound is extremely favorable. Thus, the resulting hydrogel material 20 and the hydrogel material layer 22 provide a bio-compatible, non-irritating, fluid absorbing, bacterial protective, cushioning, skin-like media over the burn site. An additional advantage of the hydrogel material 20 and the hydrogel material layer 22 is that they are both transparent, making it possible to inspect the burn site without removing the burn dressing, provided the bacterial barrier layer 14, the bonding layer 16, and the impregnated layer 18 are all transparent as well.

It has been found that a more preferred hydrogel composition for the hydrogel material 20 is formed from an aqueous mixture including from about 0% to about 90% by weight polyhydric alcohol; from about 6% to about 60% by weight aliphatic diisocyanate terminated prepolymer; from about 4% to about 40% by weight polyethylene oxide based polyamine; up to about 2% by weight sodium chloride; and the balance water. A more preferred hydrogel composition for forming the hydrogel material 20 is formed from a mixture comprising from about 15% to about 30% by weight polypropylene glycol; from about 8% to about 14% by weight isophoronediisocyanate terminated prepolymer; from about 5% to about 10% by weight polyethylene oxide based diamine; and up to about 1% by weight sodium chloride; and the balance water. Most preferably, the hydrogel material 20 is formed from a mixture comprising: (a) from about 16% to 17% by weight polypropylene glycol; (b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The preferred aliphatic diisocyanate terminated prepolymer is an isophoronediisocyanate terminated prepolymer based on polyols containing more than about 40% polyethylene oxide and having an isocyanate content of about 3% by weight. The molecular weight of the isophoronediisocyanate terminated prepolymer is preferably in a range from about 1500 to about 8000 and most preferably, from about 4000 to about 5000. The polyethylene oxide based polyamine is preferably a polyethylene oxide based diamine having a molecular weight in a range from about 200 to about 6000 and most preferably, about 2000. It is also preferable that the aliphatic diisocyanate terminated prepolymer and the polyethylene oxide based polyamine have a stoichiometric ratio of about 1:1. Those skilled in the art will appreciate that all of the constituents with the preferred hydrogel material may be readily synthesized or purchased commercially neither of which is more preferred. The aforementioned preferred hydrogel compositions provide a burn dressing product 10 having the desired properties of excellent biocompatibility and absorption of exudate properties without adhering to the wound. However, other materials having such characteristics, including but not limited to the aforementioned hydrogel compositions, may be used to form the hydrogel material 20 in accordance with the present invention.

The following examples are provided for purposes of illustrating the new and unexpected absorbency characteristics of the hydrogel material 20 formed in accordance with the present invention. Such examples should not be regarded in any way as limiting the scope of invention as defined in the claims appended hereto.

EXAMPLE I

A mixture of 15.4% by weight polypropylene glycol; 15.05% by weight isophoronediisocyanate terminated prepolymer; 9.95% by weight polyethylene oxide based diamine; 1% by weight sodium chloride; and 58.6% by weight water was poured into a 4"×4" mold and allowed to cure. The resulting hydrogel material was then irradiated at 2.5 Mrads for purposes of sterilization only as the hydrogel material does not require irradiation for curing. Thereafter, the hydrogel material was immersed in a 190×100 mm crystallizing dish containing 500 ml of 0.9% NaCl solution representative of wound exudate. The weight of the hydrogel material after it had been removed from the saline solution was measured at various times as shown in Table I below. The initial weight refers to the dry weight of the hydrogel material and the prewetted weight refers to the weight of the hydrogel material after it had been initially immersed in the saline solution and instantaneously removed. The prewetted weight provides the most accurate basis from which to calculate the percentage weight increase in that when the hydrogel material is removed at various progressive time periods, an amount of saline solution remains on the hydrogel material which can be equated with the difference between the dry hydrogel weight and the prewetted weight. Accordingly, in order to take into account for this amount of saline solution remaining on the hydrogel material after it has been removed, the percentage weight increase was calculated based upon the prewetted weight in Table I as well as Tables II-VI.

TABLE I

| Time | Weight | % Increase over original weight |
|---|---|---|
| Initial | 19.22 g | |
| Prewetted | 20.03 g | |
| 1.25 hrs. | 30.28 g | 51% |
| 2.00 hrs. | 34.34 g | 71% |
| 3.00 hrs. | 38.12 g | 90% |
| 4.00 hrs. | 41.76 g | 108% |
| 5.00 hrs. | 43.84 g | 119% |
| 6.00 hrs. | 45.39 g | 127% |
| 7.00 hrs. | 47.58 g | 138% |
| 8.00 hrs. | 49.59 g | 148% |
| 24.00 hrs. | 61.42 g | 207% |
| 48.00 hrs. | 65.90 g | 229% |

As can be seen in Table I, the hydrogel material of Example I possesses extremely desirable absorbency characteristics with respect to the NaCl solution which was new and unexpected. Thus, such a hydrogel material performs the desired objectives of wound dressings and is particularly useful in burn dressings.

EXAMPLE II

A mixture of 18.4% by weight polypropylene glycol; 12.5% by weight isophoronediisocyanate terminated prepolymer; 9.0% by weight polyethylene oxide based diamine; 0.0% by weight sodium chloride; and 60.1% by weight water was poured into a 4"×4" mold an allowed to cure. The resulting hydrogel material was then irradiated at 2.5 Mrads for purposes of sterilization only as the hydrogel material does not require irradiation for curing. Thereafter, the hydrogel material was immersed in a 190×100 mm crystallizing dish containing 500 ml of 0.9% NaCl solution representative of wound exudate. The weight of the hydrogel material after it had been remove from the saline solution was measured at various times as described above and shown in Table II below.

TABLE II

| Time | Weight | % Increase over original weight |
| --- | --- | --- |
| Initial | 18.10 g | |
| Prewetted | 19.44 g | |
| 1.25 hrs. | 29.59 g | 52% |
| 2.00 hrs. | 33.32 g | 71% |
| 3.00 hrs. | 35.83 g | 84% |
| 4.00 hrs. | 38.84 g | 100% |
| 5.00 hrs. | 40.79 g | 110% |
| 6.00 hrs. | 41.92 g | 117% |
| 7.00 hrs. | 44.13 g | 127% |
| 8.00 hrs. | 46.17 g | 138% |
| 24.00 hrs. | 53.06 g | 173% |
| 48.00 hrs. | 57.49 g | 196% |

As can be seen in Table II, the hydrogel material of Example II also possesses extremely desirable absorbency characteristics which was new, unexpected and superior to those materials used in the past. Therefore, the hydrogel material of Example II performs the desired objectives of wound dressings in accordance with the invention.

EXAMPLE III

A mixture of 52.7% by weight polypropylene glycol; 14.8% by weight isophoronediisocyanate terminated prepolymer; 9.5% by weight polyethylene oxide based diamine; 0.2% by weight sodium chloride; and 22.8% by weight water was poured into a 4"×4"mold and allowed to cure. The resulting hydrogel material was then irradiated at 2.5 Mrads for purposes of sterilization only as the hydrogel material does not require irradiation for curing. Thereafter, the hydrogel material was immersed in a 190×100 mm crystallizing dish containing 500 ml of 0.9% NaCl solution representative of wound exudate. The weight of the hydrogel material was measured at various times as described above and which is shown in Table III below.

TABLE III

| Time | Weight | % Increase over original weight |
| --- | --- | --- |
| Initial | 13.93 g | |
| Prewetted | 14.89 g | |
| 1.25 hrs. | 27.05 g | 82% |
| 2.00 hrs. | 30.49 g | 105% |
| 3.00 hrs | 33.76 g | 127% |
| 4.00 hrs. | 36.10 g | 142% |
| 5.00 hrs. | 37.24 g | 150% |
| 6.00 hrs. | 38.51 g | 159% |
| 7.00 hrs. | 39.36 g | 164% |
| 8.00 hrs. | 40.10 g | 169% |
| 24.00 hrs. | 45.52 g | 206% |
| 48.00 hrs. | 46.75 g | 214% |

As can be seen in Table III, the hydrogel material of Example III possesses extremely desirable absorbency characteristics superior to those of the previous examples. Such a result was new and unexpected. The hydrogel material of Example III is the most preferred in that it has the capability of absorbing the most wound exudate in the shortest period of time.

EXAMPLE IV

A mixture of 63.6% by weight polypropylene glycol; 16.4% by weight isophoronediisocyanate terminated prepolymer; 10.2% by weight polyethylene oxide based diamine; and 9.8% by weight water was poured into a 4"×4" mold and allowed to cure. The resulting hydrogel material was then irradiated at 2.5 Mrads for purposes of sterilization only as the hydrogel material does not require irradiation for curing. Thereafter, the hydrogel material was immersed in a 190×100 mm crystallizing dish containing 500 ml of 0.9% NaCl solution representative of wound exudate. The weight of the hydrogel material was measured at various times as described above and which is shown in Table IV below.

TABLE IV

| Time | Weight | % Increase over original weight |
| --- | --- | --- |
| Initial | 14.69 g | |
| Prewetted | 15.81 g | |
| 1.25 hrs. | 27.77 g | 76% |
| 2.00 hrs. | 31.72 g | 101% |
| 3.00 hrs. | 34.17 g | 116% |
| 4.00 hrs. | 36.31 g | 130% |
| 5.00 hrs. | 37.82 g | 139% |
| 6.00 hrs. | 39.04 g | 147% |
| 7.00 hrs. | 40.21 g | 154% |
| 8.00 hrs. | 41.75 g | 164% |
| 24.00 hrs. | 46.78 g | 196% |
| 48.00 hrs. | 48.48 g | 207% |

As can be seen in Table IV, the hydrogel material of Example IV possesses extremely desirable absorbency characteristics extremely useful in the treatment of wounds. Such a result was new and unexpected.

EXAMPLE V

A mixture of 16.0% by weight polypropylene glycol; 13.3% by weight isophoronediisocyanate terminated prepolymer; 9.5% by weight polyethylene oxide based diamine; 0.9% by weight sodium chloride; and 60.3% by weight water was poured into a 4"×4" mold and allowed to cure. The resulting hydrogel material was then irradiated at 2.5 Mrads for purposes of sterilization only as the hydrogel material does not require irradiation for curing. Thereafter, the hydrogel material was immersed in a 190×100 mm crystallizing dish containing 500 ml of 0.9% NaCl solution representative of wound exudate. The weight of the hydrogel material was measured at various times as described above and which is shown in Table V below.

TABLE V

| Time | Weight | % Increase over original weight |
| --- | --- | --- |
| Initial | 18.93 g | |
| Prewetted | 19.66 g | |
| 1.00 hrs. | 10.04 g | 53% |
| 2.00 hrs. | 14.02 g | 74% |
| 3.00 hrs. | 15.89 g | 84% |
| 6.50 hrs. | 20.20 g | 107% |

As can be seen in Table V, the hydrogel material of Example V possesses superior absorbency characteristics as compared to those used in the past. The hydrogel material as prepared in Example V also finds excellent utility in the treatment of wounds such as burns and the like.

EXAMPLE VI

A mixture of 16.4% by weight polypropylene glycol; 12.8% by weight isophoronediisocyanate terminated prepolymer; 9.2% by weight polyethylene oxide based diamine; 0.9% by weight sodium chloride; and 60.7% by weight water was poured into a 4"×4" mold and allowed to cure. The resulting hydrogel material was then irradiated at 2.5 Mrads for purposes of sterilization only as the hydrogel material does not require irradiation for curing. Thereafter, the hydrogel material was then placed in an oven at 130° F. for 3.5 hours to evaporate some of the water contained in the hydrogel material. After the hydrogel material was removed from the oven, the hydrogel material experienced a weight reduction of approximately 45% attributed entirely to water loss. The hydrogel material was then immersed in a 190×100 mm crystallizing dish containing 500 ml of 0.9% NaCl solution representative of wound exudate. The weight of the hydrogel material was measured at various times as described above and which is shown in Table VI below.

TABLE VI

| Time | Weight | % Increase over original weight |
|---|---|---|
| Initial | 16.17 g | |
| After Drying | 8.57 g | (45%) |
| Prewetted | 9.40 g | |
| 1.25 hrs. | 23.26 g | 162% |
| 1.75 hrs. | 25.31 g | 186% |
| 2.75 hrs. | 28.36 g | 221% |
| 3.75 hrs. | 30.19 g | 243% |
| 5.00 hrs. | 32.18 g | 266% |
| 6.00 hrs. | 33.56 g | 282% |
| 7.00 hrs. | 34.99 g | 299% |

As can be seen in Table VI, the hydrogel material of Example IV possesses extremely desirable absorbency characteristics superior to those used in the past. Such a result was new and unexpected.

Referring now to FIGS. 4A–4D, a preferred method of application of the burn dressing product 10 is illustrated in sequence. FIG. 4A illustrates how the release liner 24 can be gripped by the person applying the burn dressing product 10, to begin removal of the release liner 24 and expose the hydrogel material layer 22 before the burn dressing product 10 is applied to the burn site. In FIG. 4B, the burn dressing product 10 has been flipped over so the hydrogel material layer 22 can contact the burn site 30. The release liner 24 continues to be removed in a rolling motion as the hydrogel material layer 22 is placed over the burn site 30. Once the release liner 24 has been completely removed and the remaining layers of the burn dressing product 10 are properly situated over the burn site 30, the burn dressing product 10 is secured to the burn site 30 by gently pressing into place the burn dressing product 10, as illustrated in FIG. 4C. Finally, in one embodiment, as shown in FIG. 4D, if the dimensionally stable backing member 26 is used, it is peeled away from the bacterial barrier layer 14, to leave only the burn dressing 12 on the burn site 30.

Once the dimensionally stable backing member 26 has been completely removed, or if the dimensionally stable backing member is not used in the embodiment, only the bacterial barrier layer 14, the impregnated layer 18, and the hydrogel material layer 22, remain on the burn site 30. The result is a burn dressing 12 containing a burn healing hydrogel material layer 22 which gently contacts the burn site 30.

The burn dressing product 10 of the present invention is particularly advantageous for use on exuding burns. In particular, a special feature of the hydrogel material layer 22 is that it retains its gel integrity even upon removal of the burn dressing 12 from a burn site. The hydrogel material layer 22 does not leave debris in the burn when the burn dressing is removed, nor does it adhere to the burn site. The benefit of this feature is that the hydrogel material layer 22 exhibits a capability of non-traumatically releasing from the burn when the burn dressing 12 is removed, so as not to destroy new cell tissue forming at the burn site. Thus, healing is not inhibited by removal of the dressing 12.

Having described the invention in detail and by reference to preferred embodiments thereof, it will be apparent that modifications and variations are possible without departing from the scope of the invention which is defined in the appended claims.

What is claimed is:

1. A hydrogel composition for use in a wound dressing formed form a mixture comprising:
   (a) from about 0% to about 90% by weight polyhydric alcohol;
   (b) from about 6% to about 60% by weight isophoronediisocyanate terminated prepolymer;
   (c) from about 4% to about 40% by weight polyethylene oxide based polyamine;
   (d) 0% to about 2% by weight sodium chloride; and
   (e) the balance water.

2. The hydrogel composition of claim 1 wherein said mixture comprises:
   (a) from about 15% to about 30% by weight polyhydric alcohol;
   (b) from about 8% to about 14% by weight isophoronediisocyanate terminated prepolymer;
   (c) from about 5% to about 10% by weight polyethylene oxide based diamine;
   (d) up to about 1% by weight sodium chloride; and
   (e) the balance water.

3. The hydrogel composition of claim 1 wherein said mixture comprises:
   (a) from about 16% to about 17% by weight polypropylene glycol;
   (b) from about 10% to 12% by weight isophoronediisocyanate terminated prepolymer;
   (c) from about 7% to 9% by weight polyethylene oxide based diamine;
   (d) about 0.5% to 1% by weight sodium chloride; and
   (e) the balance water.

4. The hydrogel composition of claim 1 wherein said aliphatic diisocyanate terminated prepolymer is an isophoronediisocyanate based on polyols containing more than about 40% polyethylene oxide and having an isocyanate content of about 3% by weight.

5. The hydrogel composition of claim 4 wherein the molecular weight of said isophoronediisocyanate terminated prepolymer is in a range from about 1500 to about 8000.

6. The hydrogel composition of claim 1 wherein said polyethylene oxide based polyamine is a polyethylene oxide based diamine having a molecular weight in a range from about 200 to about 6000.

7. The hydrogel composition of claim 1 wherein said aliphatic diisocyanate terminated prepolymer and said polyethylene oxide based polyamine have a stoichiometric ratio of about 1:1.

8. The hydrogel composition of claim 1 wherein said mixture is transparent so as to permit visual inspection of a wound to which said hydrogel composition is adhered.

9. The hydrogel composition of claim 1 wherein said polyhydric alcohol is polypropylene glycol.

10. A hydrogel composition for use in a wound dressing formed from a mixture comprising:
   (a) from about 0% to about 90% by weight polyhydric alcohol selected form the group consisting of polypropylene glycol, polyethylene glycol and glycerine;
   (b) from about 6% to about 60% by weight isophoronediisocyanate terminated prepolymer based on polyols containing more than about 40% polyethylene oxide and having an isocyanate content of about 3% by weight;
   (c) from about 4% to about 40% by weight polyethylene oxide based diamine;
   (d) up to about 2% by weight sodium chloride; and
   (e) the balance water.

11. The hydrogel composition of claim 10 wherein said isophoronediisocyanate terminated prepolymer has a molecular weight of about 4000–5000.

12. The hydrogel composition of claim 10 wherein said polyethylene oxide based diamine has a molecular weight in a range from about 2000.

13. The hydrogel composition of claim 10 wherein said mixture comprises:
   (a) about 52.7% by weight polypropylene glycol;
   (b) about 14.8% by weight isophoronediisocyanate terminated prepolymer;
   (c) about 9.5% by weight polyethylene oxide based diamine;
   (d) about 0.2% by weight sodium chloride; and
   (e) about 22.8% by weight water.

14. The hydrogel composition of claim 10 wherein said isophoronediisocyanate terminated prepolymer and said polyethylene oxide based diamine have a stoichiometric ratio of about 1:1.

15. The hydrogel composition of claim 10 wherein said mixture is transparent so as to permit visual inspection of a wound to which said hydrogel composition is adhered.

16. The hydrogel composition of claim 10 wherein said polyhydric alcohol is polypropylene glycol.

17. A hydrogel composition formed from a mixture comprising:
   (a) from about 15% to about 30% by weight polyhydric alcohol selected from the group consisting of polypropylene glycol, polyethylene glycol and glycerine;
   (b) from about 8% to about 14% by weight isophoronediisocyanate terminated prepolymer based on polyols containing more than about 40% polyethylene oxide and having an isocyanate content of about 3% by weight;
   (c) from about 5% to about 10% by weight polyethylene oxide based diamine, said isophoronediisocyanate terminated prepolymer and said polyethylene oxide based diamine having a stoichiometric ratio of about 1:1;
   (d) up to about 1% by weight sodium chloride; and
   (e) the balance water.

18. The hydrogel composition of claim 17 wherein the molecular weight of said isophoronediisocyanate terminated prepolymer is in a range from about 1500 to about 8000.

19. The hydrogel composition of claim 17 wherein the molecular weight of said polyethylene oxide based diamine is in a range from about 200 to about 6000.

* * * * *